(12) United States Patent
Kux et al.

(10) Patent No.: US 8,658,143 B2
(45) Date of Patent: Feb. 25, 2014

(54) OPTICALLY APPEALING COSMETIC OR DERMATOLOGICAL PREPARATION

(75) Inventors: Ulrich Kux, Hamburg (DE); Ulrike Schulz, Hamburg (DE); Stefan Biel, Hamburg (DE); Sabine Ripke, Hamburg (DE); Lara Terstegen, Hamburg (DE)

(73) Assignee: Beiersdorf AG, Hamburg (DE)

( * ) Notice: Subject to any disclaimer, the term of this patent is extended or adjusted under 35 U.S.C. 154(b) by 938 days.

(21) Appl. No.: 11/586,585

(22) Filed: Oct. 26, 2006

(65) Prior Publication Data

US 2007/0116656 A1 May 24, 2007

(30) Foreign Application Priority Data

Nov. 18, 2005 (DE) .......... 10 2005 055 519

(51) Int. Cl.
*A61K 8/00* (2006.01)
*A61K 8/18* (2006.01)
*A61Q 15/00* (2006.01)
*A61K 9/00* (2006.01)

(52) U.S. Cl.
USPC .......................................... 424/65; 424/400

(58) Field of Classification Search
USPC .......................................................... 424/65
See application file for complete search history.

(56) References Cited

U.S. PATENT DOCUMENTS

| | | | |
|---|---|---|---|
| 3,509,253 A | | 4/1970 | Babbin |
| 3,920,883 A * | | 11/1975 | Yamada et al. ............ 514/762 |
| 3,991,176 A * | | 11/1976 | Rubino ....................... 424/47 |
| 5,318,778 A | | 6/1994 | Schmucker et al. |
| 5,374,614 A | | 12/1994 | Behan et al. |
| 5,587,153 A | | 12/1996 | Angelone, Jr. et al. |
| 5,648,067 A | | 7/1997 | Dillenburg et al. |
| 5,718,888 A | | 2/1998 | Klier et al. |
| 5,863,525 A | | 1/1999 | Angelone, Jr. et al. |
| 5,925,338 A | | 7/1999 | Karassik et al. |
| 5,955,060 A | | 9/1999 | Hüglin et al. |
| 5,962,452 A | | 10/1999 | Haase et al. |
| 6,042,816 A | | 3/2000 | Shen |
| 6,245,325 B1 | | 6/2001 | Shen |
| 6,248,311 B1 | | 6/2001 | Candau |
| 6,468,551 B1 | | 10/2002 | Diec et al. |
| 6,607,733 B1 | | 8/2003 | Diec et al. |
| 7,294,330 B2 * | | 11/2007 | Banowski et al. ........... 424/65 |
| 2003/0147963 A1 | | 8/2003 | De Moragas et al. |
| 2004/0047822 A1 | | 3/2004 | Zamudo-Tena et al. |
| 2004/0228886 A1 * | | 11/2004 | Ding et al. ............... 424/401 |
| 2004/0234466 A1 | | 11/2004 | Banowski et al. |
| 2004/0247547 A1 | | 12/2004 | Kux et al. |
| 2004/0253187 A1 | | 12/2004 | Kux et al. |
| 2005/0048013 A1 | | 3/2005 | Diec et al. |
| 2007/0218025 A1 * | | 9/2007 | Schulz et al. ............. 424/68 |

FOREIGN PATENT DOCUMENTS

| | | |
|---|---|---|
| EP | 0571677 | 5/1992 |
| EP | 1787629 | 5/2007 |
| GB | 2280111 | 1/1995 |
| WO | 92/05767 | 4/1992 |
| WO | 96/28132 | 9/1996 |
| WO | 98/32418 | 7/1998 |
| WO | 00/10512 | 3/2000 |

OTHER PUBLICATIONS

English Language Abstract of EP 0 775 486, May 28, 1997.
English Language Abstract of DE 198 57 235, Jun. 15, 2000.
English Language Abstract of EP 0 925 783, Jun. 30, 1999.
English Language Abstract of DE 40 09 347, Sep. 26, 1991.
English Language Abstract of DE 37 40 186, Jan. 5, 1989.
English Language Abstract of DE 42 04 321, Aug. 19, 1993.
English Language Abstract of DE 42 29 707, Mar. 10, 1994.
English Language Abstract of DE 42 29 737, Mar. 10, 1994.
English Language Abstract of DE 43 24 219, Jan. 26, 1995.
English Language Abstract of DE 100 47 448, May 2, 2002.
English Language Abstract of WO 2005/105026.
English Language Abstract of WO 2005/102256.
English Language Abstract of WO 03/053388.
English Language Abstract of WO 98/15255.

\* cited by examiner

*Primary Examiner* — Mina Haghighatian
*Assistant Examiner* — Luke Karpinski
(74) *Attorney, Agent, or Firm* — Abel Law Group, LLP

(57) ABSTRACT

A cosmetic or dermatological preparation which comprises an aluminum containing antiperspirant active ingredient, an α-hydroxycarboxylic acid, water and optionally, a plurality of particles in a stably suspended state. This Abstract is not intended to define the invention disclosed in the specification, nor intended to limit the scope of the invention in any way.

38 Claims, No Drawings

OPTICALLY APPEALING COSMETIC OR DERMATOLOGICAL PREPARATION

CROSS-REFERENCE TO RELATED APPLICATIONS

The present application claims priority under 35 U.S.C. §119 of German Patent Application 10 2005 055 519.5, filed Nov. 18, 2005, the entire disclosure whereof is expressly incorporated by reference herein.

BACKGROUND OF THE INVENTION

1. Field of the Invention

The present invention relates to an aqueous cosmetic or dermatological preparation which preferably comprises particles in a suspended state.

2. Discussion of Background Information

For aesthetic reasons in particular, transparent and translucent products are preferred by many consumers. Thus, transparent formulations are often used, for example, as deodorant or antiperspirant (AP). These can nowadays be realized by the following technologies:
1. aqueous-alcoholic formulations
2. water-in-silicone emulsions
3. microemulsions Aqueous-alcoholic deodorant and AP formulations are mostly based on water and alcohol as medium, deodorant and antiperspirant agents as active ingredients, and also perfume, solubilizers and thickeners (mostly based on carbohydrate) as additional agents. They are perceived by the consumer as being fresh and cooling, but are at the same time encumbered with a whole series of disadvantages. Thus, for example, application primarily to freshly shaved skin is associated with incompatibilities as a result of the alcohol content. Another major disadvantage is the fact that relatively large amounts of oil cannot be incorporated into such systems. As a result of the high content of antiperspirant salt required for highly effective performance, a white residue remains following application to the skin; this is perceived by the consumer as being extremely troublesome. However, due to the absence of a sufficiently large oil phase for technical reasons, this residue cannot be concealed. Moreover, the use of carbohydrate thickeners leads to high stickiness of the product after the alcohol has evaporated.

Water-in-silicone emulsions belong to the group of water-in-oil emulsions. The water phase comprising ethanol or polyhydric alcohols, such as, for example, propylene glycol and water-soluble active ingredients, such as AP agent and/or deodorant active ingredient, constitutes about 75-90% of the formulation. The oil phase consists of a volatile and a non-volatile silicone oil and also a silicone emulsifier.

The transparency of water-in-silicone emulsions is based on matching the refractive indices of the two phases. It is a drawback that even a difference in the indices of 0.0004 caused, for example, by evaporation, leads to cloudiness. WO 98/32418 and WO 92/05767, the entire disclosures whereof are expressly incorporated by reference herein, describe such deodorant or AP formulations based on W/S emulsions.

One approach for solving the described disadvantages has been made possible through cosmetically pleasing alcohol-free and transparent products which are based on so-called microemulsions. These have the major advantage that even relatively large amounts of various oils—with all of the described positive effects for the consumer—can be stably incorporated. Formulations of this type are in principle available by means of phase inversion temperature technology (PIT) or high-pressure homogenization. The required stability of the emulsifier system to high concentrations of antiperspirant salts, however, places high demands on the formulation skill of the product developer.

WO 98/15255, the entire disclosure whereof is expressly incorporated by reference herein, describes microemulsions. However, a drawback even with these formulations is a sticky feel on the skin caused by the thickener, and the lack of a yield point.

In view of the foregoing, it would be advantageous to have available a cosmetic or dermatological preparation which is transparent or translucent and preferably exhibits low, if any, stickiness. In particular, it would be desirable to provide a cosmetic or dermatological preparation which is transparent and has no cloudiness at all, is characterized by a minimized stickiness and has a defined yield point for optimized discharge and application.

In the field of antiperspirants it is customary to increase the amount of antiperspirant active ingredient, such as, for example, aluminum chlorohydrates (ACH) to increase the antiperspirant effectiveness. Furthermore, so-called activated aluminum chlorohydrates (AACH) are known as antiperspirant active ingredients with increased effectiveness, see, e.g., EP 925783 or Antiperspirants and Deodorants, 2nd Edition, Cosmetic and Technology Science, Vol. 20, 1999. The entire disclosures of these documents are expressly incorporated by reference herein.

However, by increasing the amount of active ingredient the antiperspirant effectiveness can be increased to only a limited degree because above a content of about 15% by weight of the AP active ingredient, saturation of the effectiveness is established and in addition disadvantages such as white residues and an unpleasant feel on the skin are increased.

If an aluminum salt $AlX_3$ of a strong acid (e.g. $AlCl_3$) is dissolved in water, then, in accordance with the equation:

$$AlX_3 + 6H_2O \rightarrow Al(H_2O)_6^{3+} + 3X^-$$

the octahedral hexaaquaaluminum ion $[Al(H_2O)_6]^{3+}$ is formed, which acts as a weak cationic acid.

As a consequence of the acidic effect, the hexaaquaaluminum ion is liable to hydrolysis and can be successively deprotonated to form the hexahydroxoaluminate ion $[Al(OH)_6]^{3-}$.

Depending on the pH and the concentration of aluminum ions, three-dimensional structures are formed as a result of bridging with hydroxide ions and oxygen atoms. These processes, in which element atoms are bridged by hydroxide ions, are called olation and for bridges with oxide ions, the term used is oxolation.

Both reactions belong to the group of condensation reactions.

The polynuclear aluminum cations $[Al_m(OH)_n(H_2O)_o]^{p+}$ which are present in aqueous aluminum salt solutions belong to the group of isopolyoxo cations.

In order to achieve an increased antiperspirant effectiveness of classic aluminum chlorohydrate (ACH) solutions, the solutions may be thermally treated by using suitable concentration, temperature and pressure ranges, and the resulting solutions may be dried by means of spray-drying. This leads to an increased amount of molecules of smaller size being present in stable form. However, in water these activated aluminum complex salts (AACH) which are effective as antiperspirants disintegrate back to their original equilibrium state, thereby losing their increased effectiveness.

Use of these activated ACH (AACH) types has therefore hitherto only made sense in nonaqueous systems since otherwise reconversion to the molecular size distribution as occurs in classic ACH solutions is likely to occur, as described, for example, in the article by A. H. Rosenberg—Antitranspirant Technology, SÖFW-Journal, 128 (4) 2000, the entire disclosure whereof is expressly incorporated by reference herein.

It would be desirable to provide an aqueous cosmetic or dermatological preparation without the described disadvantages. In particular, it would be advantageous to have available aqueous cosmetic or dermatological preparations which, despite their water content, comprise a significant concentration of activated aluminum complex salts.

Additives are often added to cosmetic or dermatological preparations such as, e.g., antiperspirant formulations in order to increase the convenience or optical acceptance.

However, it is often impossible to incorporate suitable visible particles in stabilized form such that the particles do not sink, particularly in the case of a relatively long standing time, and do not mix with the remaining constituents of the formulation.

It would therefore also be desirable to provide a cosmetic or dermatological preparation which makes it possible to incorporate particles in stably suspended form without the particles sinking, particularly in the case of a relatively long standing time, or the particles mixing with the remaining constituents of the preparation into which they are incorporated.

SUMMARY OF THE INVENTION

The present invention provides a cosmetic or dermatological preparation which comprises (a) at least one antiperspirant active ingredient, (b) at least one α-hydroxycarboxylic acid, (c) water and (d) optionally, a plurality of particles in a suspended state.

In one aspect of the preparation, the plurality of particles may be seen with the naked eye.

In another aspect, at least about 98% of the particles may have a size which does not exceed about 5 mm, e.g., does not exceed 2 mm.

In another aspect, the particles may comprise a solid and/or they may comprise a liquid (such as, e.g., an emulsion) and/or they may comprise a gas (such as, e.g., air). Further, the particles may be uncoated and/or they may be colored.

In yet another aspect of the preparation, component (b) may comprise mandelic acid and/or component (a) may comprise one or more aluminum salts such as, e.g., aluminum chlorohydrate and activated aluminum chlorohydrate.

In another aspect, the weight ratio of components (a) and (b) may be from about 15:1 to about 1:1, e.g., from about 12:1 to about 2:1.

In a still further aspect of the preparation, component (a) may be present in an amount of from about 1% to about 35% by weight, e.g., from about 1% to about 25% by weight and/or component (b) may be present in an amount of from about 0.1% to about 10% by weight, e.g., from about 0.1% to about 8% by weight, each based on the total weight of the preparation.

In another aspect, the preparation may comprise an O/W microemulsion. The microemulsion may comprise one or more emulsifiers which are at least one of polyethoxylated and polypropoxylated.

In yet another aspect, the preparation may comprise a gel.

In another aspect, the preparation may have a defined yield point. For example, the preparation may have a yield point, determined at 25° C. with a shear stress time ramp of 40 Pa/min, of from about 5 Pa to about 120 Pa, e.g., from about 10 Pa to about 120 Pa, or from about 40 Pa to about 100 Pa.

In another aspect, the preparation may be transparent or translucent.

In yet another aspect, the preparation may further comprise a sunscreen and/or the preparation may further comprise EDTA and/or a salt thereof (e.g. a sodium salt thereof) and/or the preparation may further comprise a perfume and a solubilizer for the perfume. The solubilizer may comprise a polyalkoxylated (e.g., polyethoxylated) fatty acid triglyceride.

The present invention also provides a cosmetic or dermatological preparation which comprises (a) activated aluminium chlorohydrate, (b) mandelic acid, (c) water and (d) optionally, a plurality of particles in a suspended state.

In one aspect, the weight ratio of (a): (b) may be from about 10:1 to about 2.5:1.

In another aspect, the preparation may comprise from about 1% to about 20% by weight of (a) and from about 0.1% to about 8% by weight of (b), based on the total weight of the preparation.

In another aspect, the preparation may comprise an O/W microemulsion. For example, the microemulsion particles may have a yield point of from about 0.5 Pa to about 300 Pa.

In yet another aspect, the preparation may comprise a microemulsion gel.

The present invention also provides a combination of a preparation of the present invention as set forth above, including the various aspects thereof, and an applicator for the preparation. The applicator is suitable for applying the preparation onto the skin and comprises a rotatable and rotationally symmetric body with a structured surface such as, e.g., a ball with a structured surface.

The present invention also provides a glass container which is partially or completely filled with a preparation of the present invention as set forth above, including the various aspects thereof.

In one aspect, the container may be associated with an applicator which is suitable for applying the preparation onto skin and comprises a rotatable and rotationally symmetric body with a structured surface.

The present invention also provides a method of caring for skin or protecting skin e.g., face skin. The method comprises applying to the skin the preparation of the present invention as set forth above, including the various aspects thereof.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

It is surprising that a composition comprising at least one aluminum compound (which will usually be capable of exhibiting antiperspirant activity), at least one α-hydroxycarboxylic acid, preferably mandelic acid, and water permits the provision of a transparent or translucent, low-stick cosmetic or dermatological preparation (such as, e.g., an antiperspirant preparation) which is capable of having particles stably suspended therein.

As used herein and in the appended claims, the term "particles" is meant to include any liquid, solid, semisolid or gaseous matter which is present in particulate form such as, e.g., in the form of (solid or semisolid) grains, beads, flakes, fibers (micro)spheres, liquid drops (comprising, for example, neat liquids, solutions, emulsions, dispersions, etc.) and gas (e.g., air, carbon dioxide, nitrogen, oxygen, etc.) bubbles. The solid or semisolid particles may, for example, be solid particles, hollow (i.e., gas filled) particles (e.g., hollow microspheres) or hollow particles which are completely or partially filled with one or more solid, semisolid or liquid substances (such as, e.g., microcapsules). For example, they may impart one or more of sparkle, pearlescence, color and reflectivity to the preparation.

The particles may be hard, soft, of regular shape (e.g., round or oval), of irregular shape, colored (e.g., blue, red, green, orange, purple, pink and yellow and any mixtures thereof) black or uncolored (white). They may be present in the preparation in any concentration, preferably in a concentration of at least about 0.001% by volume, e.g., at least about 0.01% by volume, at least about 0.1% by volume, or at least about 1% by volume, relative to the total volume of the (preferably liquid) preparation. The particle concentration will usually be not higher than about 50% by volume, e.g., not higher than about 30% by volume, not higher than about 20% by volume or not higher than about 10% by volume of the total volume of the preparation.

Also, the particles may comprise any constituents, particularly those which are suitable for use in cosmetic or dermatological preparations. By way of non-limiting example, they may comprise one or more substances selected from preservatives, bactericides, (inorganic and organic) UV filter substances, antioxidants, (preferably water-soluble) vitamins, mineral substances, cosmetically or dermatologically active substances, perfumes, antifoaming agents, dyes, (coloring) pigments, emollients, moisturizers, humectants, deodorizers, opacifiers, binders, buffering agents, chelating agents, viscosity controlling agents, emulsifiers, emulsion stabilizers, film formers, organic solvents (e.g., alcohols, polyols), foam stabilizers, fats, oils, waxes and/or silicone derivatives. Of course, any mixtures of different particles may be present as well, such as, e.g., mixtures of solid and/or semisolid particles and gaseous particles, mixtures of two or more types of solid particles of different form and/or different size and/or different composition and/or different color.

The particles preferably have a size of at least about 200 nm (e.g., at least about 500 nm, at least about 1 µm, at least about 10 µm, at least about 0.1 mm, or at least about 0.5 mm) up to several millimeters, preferably up to about 10 mm (e.g., up to about 5 mm, up to about 3 mm, up to about 2 mm or up to about 1 mm). Usually, at least about 80%, e.g., at least about 90%, at least about 95%, or at least about 98% of the particles will have a size within a particular size range, e.g., from about 0.5 mm to about 5 mm.

Non-limiting examples of particles which are suitable for use in the present invention include the gel beads which are described in U.S. 2004/0228886 A1, the entire disclosure whereof is incorporated by reference herein.

Examples of commercially available beads which are suitable for use in the present invention are available under the trade names Cosmospheres GMM-S (made by Pelletech Ltd., Switzerland; diameter 1.1-1.5 mm; green; comprising mannitol, microcrystalline cellulose, CI 77289 (Chromium Hydroxide Green) and lactic acid), Cosmospheres BMM-M (made by Pelletech Ltd., Switzerland; diameter 1.1-1.5 mm; blue; comprising mannitol, microcrystalline cellulose, CI 74160 (Pigment Blue 15) and lactic acid), Beads CosmoYS-S (made by Pelletech Ltd., Switzerland; diameter 0.5-1.0 mm; yellow; comprising lactose, microcrystalline cellulose, *Helianthus Annuus* and CI 77492); Unispheres RP-572 (available from Induchem AG, Switzerland; diameter 0.5-0.9 mm; pink; comprising lactose, cellulose, hydroxypropylmethylcellulose, panthenyl triacetate, CI 73360); Unispheres UE-507 (available from Induchem AG, Switzerland; diameter 0.5-0.9 mm; purple; comprising lactose, cellulose, hydroxypropylmethylcellulose, tocopheryl acetate, CI 77007 (Pigment Blue 29); Cosmospheres Beads BCG2-L (made by Pelletech Ltd., Switzerland; diameter 1.5-2.0 mm; blue, glittering; comprising lactose, polyethylene terephthalate, microcrystalline cellulose, Acrylates Copolymer and Pigment Blue 15) and Cosmospheres Beads WCG-G-C-L (made by Pelletech Ltd., Switzerland; diameter 1.5-2.0 mm; gold, glittering; comprising lactose, polyethylene terephthalate, microcrystalline cellulose, shellac, Acrylates Copolymer, mica, titanium dioxide and iron oxides).

If present, the particles are preferably uniformly and stably suspended in the preparation, i.e., even in the case of a relatively long standing time such as e.g., about a week or even about a month or about a year, the force of gravity does not result in the particles sinking to the bottom to any significant extent.

According to the present invention, the combination of aluminum compounds, in particular aluminum chlorohydrate (ACH) and/or activated aluminum chlorohydrate (AACH), and at least one α-hydroxycarboxylic acid, preferably mandelic acid, makes it possible to prepare aqueous, preferably transparent or translucent cosmetic or dermatological preparations which comprise stably and uniformly suspended particles therein.

Further, these preparations preferably do not exhibit any objectively or subjectively perceived stickiness.

Surprisingly, the combination according to the present invention of an AP active ingredient, α-hydroxycarboxylic acid, preferably mandelic acid, and water, it is possible to prepare formulations which have a certain yield point, which substantially prevents the particles present therein to sink or mix with the other formulation constituents (e.g., become indistinguishable from the surrounding medium) to any significant extent.

It is pointed out here that the term "antiperspirant active ingredient" as used herein is meant to encompass substances which are capable of exerting an antiperspirant effect, although this effect may not be important for the intended use of a cosmetic or dermatological preparation according to the present invention. In other words, the cosmetic or dermatological preparation according to the present invention is not necessarily intended to be an antiperspirant preparation (in fact, the preparations of the present invention are preferably different from an antiperspirant preparation and/or a deodorant preparation), but may be used and formulated for a completely different cosmetic application or a dermatological application such as, e.g., skin and hair care in the broadest sense (including, for example, face care, wrinkle reduction, skin whitening, tanning, protection from UV radiation, etc.). By way of non-limiting example, the formulations according to the present invention can, depending on their formulation, be present, as skin protection cream, face cream, cleansing milk, sunscreen lotion, nutrient cream, day or night cream, shower gels, shampoos, conditioners, hair treatments, hair rinses, hair tonics, sprays etc.

Non-limiting examples of antiperspirant active ingredients which are suitable for the purposes of the present invention include aluminum salts, in particular, acidic aluminum salts, activated acidic aluminum salts and/or aluminum/zirconium salts in aqueous solution. The concentration ranges described herein refer to the so-called active contents of the antiperspirant complexes: in the case of the aluminum compounds, to anhydrous complexes, in the case of the aluminum/zirconium compounds, to water- and buffer-free complexes. The buffer used is usually glycine.

Non-limiting examples of aluminum containing antiperspirant active ingredients which are suitable for use in the present invention include:
aluminum salts (of the empirical formula $[Al_2(OH)_mCl_n]$, where m+n=6):
  activated aluminum chlorohydrate $[Al_2(OH)_5Cl]\times H_2O$
    activated Al complexes: Reach 501 (Reheis), Aloxicoll 51 L
  activated aluminum sesquichlorohydrate $[Al_2(OH)_{4.5}Cl_{1.5}]\times H_2O$
    activated Al complexes: Reach 301 (Reheis)
aluminum-zirconium salts:
aluminum/zirconium trichlorohydrex glycine $[Al_4Zr(OH)_{13}Cl_3]\times H_2O\times Gly$
    standard Al/Zr complexes: Rezal 33GC (Reheis), AZG-7164 (Summit)
aluminum/zirconium tetrachlorohydrex glycine $[Al_4Zr(OH)_{12}Cl_4]\times H_2O\times Gly$
    standard Al/Zr complexes: Rezal 36, Rezal 36G, Rezal 36 GC (Reheis), AZG-368 (Summit), Zirkonal L435G (Giulini), Westchlor ZR 35 BX5, Westchlor ZR 41 (Westwood Chemicals)
aluminum/zirconium pentachlorohydrex glycine $[Al_8Zr(OH)_{23}Cl_5]\times H_2O\times Gly$
    standard Al/Zr complexes: Rezal 67 (Reheis), Zirkonal L540, Zirkonal L530 PG (Giulini), Westchlor ZR 80B (Westwood Chemicals)
aluminum/zirconium octachlorohydrex glycine $[Al_8Zr(OH)_{20}Cl_8]\times H_2O\times Gly$: Westchlor ZR 82B
Reach AZP—908 SUF activated Aluminum Zirconium Tetrachlorohydrex GI
Reach AZZ—902 SUF activated Aluminum Zirconium Trichlorohydrex Glyc Glycine-free aluminum/zirconium salts can be used advantageously as well.

The antiperspirant active ingredients (one or more ingredients) will usually be present in the preparation according to the present invention in an amount of at least about 1%, e.g., at least about 2%, or at least about 5% by weight, but not higher than about 35% by weight, e.g., not higher than about 25%, not higher than about 20% or not higher than about 15% by weight, based on the total weight of the preparation.

It is, of course, possible to employ both activated and nonactivated antiperspirant active ingredients and/or deodorants at the same time. For example, if both activated and non-activated aluminium compounds are used, their weight ratio is preferably from about 10:1 to about 1:10, e.g., about 1:1.

In water, the activated aluminum complex salts (e.g., AACH) decompose in a known manner back to their original equilibrium state, i.e., they are present in aqueous preparations in a non-activated state. Accordingly, use of activated ACH types (AACH) has hitherto only made sense in non-aqueous systems since otherwise reconversion to the molecular size distribution as occurs in classic ACH solutions will likely take place.

By adding α-hydroxycarboxylic acid such as mandelic acid, this reconversion can surprisingly be substantially prevented. Specifically, in the presence of α-hydroxycarboxylic acid such as mandelic acid substantially no impairment of the activation of the AACH is observed in aqueous media.

The term "α-hydroxycarboxylic acid" as used herein and in the appended claims is meant to include any (preferably aliphatic or aralphatic)) organic acid which, besides one or more COOH groups, comprises one or more OH groups in an α position relative to one of the carboxyl functionalities. These acids therefore have the properties of carboxylic acids and alcohols or phenols at the same time. The α-hydroxycarboxylic acids include naturally occurring substances, such as mandelic acid, glycolic acid, lactic acid, malic acid, tartaric acid, citric acid and other fruit acids. Usually, the α-hydroxy acids for use in the present invention will have from about 2 to about 20 carbon atoms (including the carboxylic group(s)), preferably from about 4 to about 12 carbon atoms. They usually will have 1 to about 3 carboxylic acid groups and 1 to about 3 hydroxy groups. According to the invention, all α-hydroxycarboxylic acids which are suitable for use in cosmetics may be used. Of course, mixtures of two or more α-hydroxycarboxylic acids may be used as well.

Besides enzymatic fermentation, which is used for a number of naturally occurring hydroxycarboxylic acids (e.g. for lactic acid using *Lactobacillus delbrueckii*), the synthesis of (aliphatic) α-hydroxycarboxylic acids may be accomplished, for example, by nucleophilic substitution of α-halocarboxylic acids with hydroxyl ions or from carbonyl compounds via cyanohydrins (see Scheme 1 below).

Scheme 1 - General Synthesis of α-Hydroxy Acids

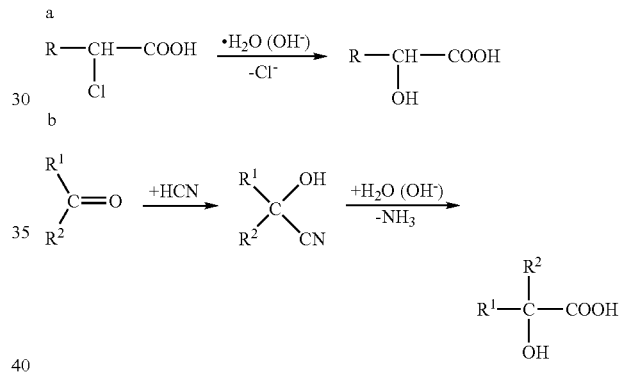

Particular preference is given to hydroxyphenylacetic acid (also called phenylglycolic acid) of the formula $H_5C_6$—CH (OH)—COOH, $C_8H_8O_3$, known under the name mandelic acid. Mandelic acid is readily soluble in water, ethanol, diethylether and 2-propanol. Synthetically, (±)-mandelic acid may be obtained from benzaldehyde and hydrocyanic acid via the corresponding α-hydroxynitrile (cyanohydrin) and acidic hydrolysis thereof corresponding to Scheme 2:

Scheme 2: Synthesis of Mandelic Acid

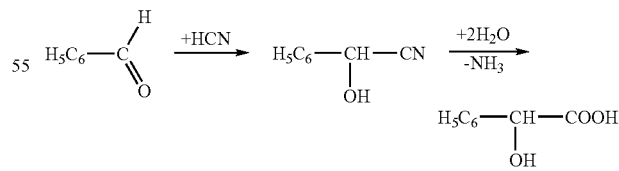

By using α-hydroxycarboxylic acids, in particular mandelic acid, in combination with aluminum containing compounds which are capable of exerting an antiperspirant activity, it is surprisingly possible to prepare cosmetic and dermatological preparations with very desirable properties, such as, for example, retention of the activated state of the activated AP ingredient, increased effectiveness, transparency and low tack and, moreover, the establishment of a defined yield point of the preparation. Furthermore, the formulation according to the invention usually is absorbed very rapidly into the skin without leaving residues behind.

The yield point is a term for the smallest shear stress above which a plastic material behaves in rheological terms like a liquid (DIN 1342-1: 1983-10, incorporated by reference herein). The yield point is determined by recording a flow curve (DIN 53019: 1980-05; DIN 53214: 1982-02, incorporated by reference herein). The value obtained is dependent on the timescale (stress rate) on which the measurement is based. This is independent of whether the measurement is carried out using a shear stress-controlled or speed-controlled viscometer. Short time scales (rapid stresses) generally produce higher values for the yield point. An excessively high yield point may be the cause of flow disturbances. On the other hand, with a suitably adjusted yield point it is possible to suppress the tendency of the liquid formulation to run.

Accordingly, a cosmetic or dermatological preparation according to the present invention is advantageously present in the form of a gel or hydrogel and preferably has a yield point, as a result of which discharge and application is improved compared to known preparations.

The preparation according to the present invention which comprises AP active ingredient, α-hydroxycarboxylic acid, in particular, mandelic acid, and water is advantageously present in the form of a transparent or translucent cosmetic or dermatological preparation. In other words, the present invention provides a water-clear and nevertheless extremely effective preparation. Usually, the preparation according to the present invention may readily be applied in gel form and results in a pleasant feel on the skin due to a substantial lack of stickiness.

In addition, the preparation according to the present invention makes it possible to incorporate particles of any size into the preparation without the particles sinking to the bottom to a significant extent even after a prolonged standing time. In addition, if the preparation has a yield point, this also ensures that the particles will not mix with the remaining constituents of the preparation to any significant extent.

It is thus possible to incorporate into the preparation, for example, cosmetic substances, such as care substances, or other cosmetically relevant and/or desirable active ingredients coloured substances which enhance the optical appearance of the preparation, and/or water-sensitive and/or hydrophobic active ingredients and care substances in cosmetically active amounts in the form of (micro)spheres or any other shapes.

The combination of α-hydroxycarboxylic acid(s), in particular mandelic acid, and AP active ingredient(s), especially aluminum salt(s) and/or activated aluminum salt(s), makes it possible to produce a hydrogel which has very desirable properties, such as transparency and low stickiness. Moreover, the preparation according to the present invention will preferably be absorbed very rapidly into the skin without leaving residues behind. Also, antiperspirants/deodorants which comprise mandelic acid have been found to usually possess a higher antitranspirant activity than comparable products without mandelic acid. Due to its keratolytic properties mandelic acid contributes to a regeneration of the skin. Moreover, mandelic acid has been found to have a bacteriostatic effect at an acidic pH.

A combination of mandelic acid and aluminum chlorohydrate (ACH) and/or activated aluminum chlorohydrate (AACH) (preferably at least ACH) where the weight ratio of aluminum chlorohydrate to mandelic acid is not higher than about 15:1, e.g., not higher than about 12:1, or not higher than about 10:1, but usually not lower than about 1:1, e.g., not lower than about 2:1, or not lower than about 2.5:1 has proven to be particularly advantageous.

The preparations according to the present invention may also be present as emulsion-based preparations.

Advantageously, the preparations according to the present invention may be based on microemulsions, preference being given to O/W microemulsions, in particular microemulsion gels, as are described in WO 98/15255 and WO 96/28132, the entire disclosures whereof are expressly incorporated by reference herein.

An emulsion-based preparation according to the present invention is preferably based on a microemulsion gel based on a microemulsions of the oil-in-water type which comprises an oil phase which is essentially comprised of one or more constituents of low volatility, and a water phase which comprises one or more polyethoxylated O/W emulsifiers and/or one or more polypropoxylated O/W emulsifiers and/or one or more polyethoxylated and polypropoxylated O/W emulsifiers and, optionally, one or more W/O emulsifiers. The total emulsifier content will usually be not higher than about 20% by weight, e.g., not higher than about 10% by weight, based on the total weight of the emulsion.

The emulsion is obtainable, for example, by bringing a mixture of the base components, comprising water phase, oil phase, one or more O/W emulsifiers and one or more optional W/O emulsifiers, and if desired further auxiliaries, additives and/or active ingredients, to a temperature within or above the phase inversion temperature range, and subsequently cooling to room temperature.

Moreover, the droplets of the discontinuous oil phase may be joined together by one or more crosslinker substances whose molecules are characterized by at least one hydrophilic region which has a size suitable for bridging the distance between the microemulsion droplets, and by at least one hydrophobic region which is able to enter into hydrophobic interaction with the microemulsion droplets.

However, the microemulsions described in WO 98/15255 and WO 96/28132 suffer from the disadvantage that a defined yield point cannot be established.

In particular, in simple emulsions, finely dispersed droplets of one phase (water droplets in the case of W/O emulsions or lipid vesicles in O/W emulsions) which are surrounded by an emulsifier sheath are present in the other phase. The droplet diameters of customary emulsions are in the range of from about 1 μm to about 50 μm. Such "macroemulsions", without further coloring additives, are milky white in color and opaque. Finer "macroemulsions" with droplet diameters in the range from about 0.1 μm to about 1 μm, are, again without coloring additives, bluish white in color and opaque.

Only micellar and molecular solutions with particle diameters of less than about 0.01 μm appear clear and transparent.

The droplet diameter of transparent or translucent microemulsions on the other hand is in the range from about $10^{-2}$ μm to about $10^{-1}$ μm. Such microemulsions are mostly of low viscosity. The viscosity of many microemulsions of the O/W type is comparable with that of water. The viscosity of these microemulsions can be increased with the help of associative thickeners, meaning that viscous gels are then present.

The preparation according to the present invention may advantageously be present in the form of a gel and preferably has a yield point as a result of which discharge and application is improved compared to known preparations.

Besides the emulsifiers known from the prior art, the emulsifiers which may particularly advantageously be used include fatty alcohol ethoxylates, such as, for example, polyethylene glycol(16) stearyl ether, fatty acid ethoxylates, such as, for example, polyethylene glycol(14) stearate, polyethylene glycol glyceryl fatty acid esters, such as, for example, polyethylene glycol(15) glyceryl laurate, and the W/O emulsifier used is, for example, glyceryl monostearate.

The oil phase preferably comprises esters of saturated and unsaturated, branched and unbranched alkanecarboxylic acids or alcohols with chain lengths of from about 12 to about 25 carbon atoms, such as, for example, octyldodecanol.

The combination according to the present invention of (optionally activated) AP active ingredient, α-hydroxycarboxylic acid (in particular, mandelic acid) and a microemulsion, in particular, a microemulsion of the type disclosed in WO 98/15255 and WO 96/28132, makes it possible to produce a transparent cosmetic or dermatological preparation with a defined yield point. The user thus has at his disposal a water-clear and nevertheless extremely effective preparation. Usually, the preparation is easy to apply in gel form and has a pleasant feel on the skin due to the substantial lack of stickiness. Preferably, it is possible to incorporate into this preparation stably and uniformly suspended particles which do not sink or mix with the emulsion to any significant extent.

Through the combination of (optionally activated) antiperspirant active ingredient and α-hydroxycarboxylic acid(s) such as mandelic acid in O/W microemulsions, it is possible to prepare transparent cosmetic formulations which have reduced or no objectively or subjectively perceived stickiness and in particular, preparations which exhibit no loss in activity of the AP component (although this activity may be of no importance for the intended use of the preparation).

Also deodorants can advantageously be added to the preparations according to the present invention, for example, those which are intended for use as antiperspirant preparations. As is the case with all other optional components of the cosmetic or dermatological preparations of the present invention, the deodorants can be present in suspended particles, if present, and/or in the medium in which the particles are suspended.

Customary cosmetic deodorants are based on various activity principles. By using antimicrobial substances in cosmetic deodorants it is possible to reduce the bacteria flora on the skin. Here, in the ideal case, only the odor-causing microorganisms should be effectively reduced. The flow of perspiration itself is not influenced as a result, in an ideal case only the microbial decomposition of the perspiration is stopped temporarily. The combination of astringents with antimicrobially effective substances in one and the same composition is also customary.

All active ingredients which are customary for deodorants can advantageously be used in the preparations of the present invention, for example, odor concealers, such as customary perfume constituents, odor absorbers, for example the sheet silicates described in DE 40 09 347, of these in particular montmorillonite, kaolinite, illite, beidellite, nontronite, saponite, hectorite, bentonite, smectite, also, for example, zinc salts of ricinoleic acid. Antimicrobial agents are likewise suitable for incorporation into the preparations according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in DE 37 40 186, DE 39 38 140, DE 42 04 321, DE 42 29 707, DE 42 29 737, DE 42 37 081, DE 43 09 372, DE 43 24 219. The entire disclosures of the above documents are incorporated by reference herein. Further examples of commercially available deodorants include phenethyl acetate, phenethyl alcohol, zinc bisgluconate, zinc dilactate, zinc dipalmitate, zinc diricinoleate and linalool. Sodium hydrogencarbonate can also be used advantageously.

The amount of deodorants (one or more compounds), if present, in the preparations of the present invention is preferably from about 0.01% to about 10% by weight, more preferably from about 0.05% to about 5% by weight, based on the total weight of the preparation.

The cosmetic and dermatological preparations according to the invention can, of course, comprise as optional components various types of cosmetic auxiliaries, especially those which are customarily used in such preparations such as, e.g. preservatives, bactericides, (inorganic and organic) UV filter substances, antioxidants, stabilizers, (preferably water-soluble) vitamins, plant extracts, mineral substances, cosmetically or dermatologically active substances (e.g., coenzyme $Q_{10}$, creatine and derivatives thereof, carnitine and derivatives thereof, licochalcones, in particular, licochalcone A), perfumes, antifoaming agents, dyes, (coloring) pigments, insect repellents, tanning agents, self-tanning agents (e.g. dihydroxyacetone), depigmenting agents (e.g. 8-hexadecene-1,16-dicarboxylic acid (dioic acid, CAS No. 20701-68-2; provisional INCI name Octadecenedioic acid)), emollients, moisturizers, humectants, re-fatting agents, opacifiers, binders, thickeners, buffering agents, pH regulators, complexing and sequestering agents, viscosity control agents, emulsifiers, emulsion stabilizers, film formers, solubilizers, antistats, electrolytes, foam stabilizers, propellants, peeling substances (abrasives, e.g. polymer beads or powders made of polyethylene, polypropylene etc. inorganic oxides, silicates etc.), fats, oils, waxes and/or silicone derivatives. If particles are present, these auxiliaries can be incorporated in the particles and/or in the medium in which the particles are suspended.

The total amount of auxiliaries in a preparation according to the present invention will usually be from about 0.001% to about 20% by weight, e.g., from about 0.01% to about 15% by weight, or from about 0.1% to about 10% by weight, based on the total weight of the preparation.

The water content of the preparations of the present invention will usually be at least about 60% by weight, e.g, at least about 70%, or at least about 80% by weight, and will usually be not higher than about 95%, e.g., not higher than about 90%, or not higher than about 85% by weight, based on the total weight of the preparation.

Of the large number of organic solvents which are conventionally used in cosmetics, ethanol is the most prevalent. Other solvents which are conventionally used in cosmetics include polyhydric alcohols such as glycerol, butylene glycol and 2-methylpentane-2,4-diol, 2-ethoxyethanol, 2-butoxyethanol, aliphatic and aromatic hydrocarbons, ethyl acetate, methyl acetate, isobutyl acetate, isopropyl acetate, propyl acetate, phenyl acetate, ethylene carbonate, propylene carbonate, butanone, and benzaldehyde.

Particularly in cases where the preparation comprises one or more perfumes (fragrance) it will often be advantageous to incorporate into the preparation one or more solubilizers for the perfume(s). Particularly advantageous solubilizers for this purpose include polyethoxylated fatty acid mono-, di- and triglycerides with a degree of ethoxylation of from about 5 to about 100, e.g., from about 20 to about 80. Particularly advantageous solubilizers include polyethoxylated hydrogenated castor oil such as, in particular, PEG-40 hydrogenated castor oil which is commercially available under various trade names (e.g., Solutor, Eumulgin, Fancol, etc.). For example, PEG-40 hydrogenated castor oil and PEG-60 hydrogenated castor oil are advantageous in that in their presence, perfumes can usually be incorporated into the present preparations in sufficient quantities (e.g., at a concentration of at least about 1% by weight, based on the total weight of the preparation) without rendering the preparation opaque and/or instable. Suitable concentrations of the solubilizer depend on, inter alia, the nature of the perfume(s) to be incorporated, but solubilizer (e.g., polyethoxylated hydrogenated castor oil) concentrations of at least about 5% by weight relative to the total weight of the preparation will usually afford very advantageous results.

Non-limiting examples of antioxidants which may be incorporated in the preparations of the present invention include amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximine, homocysteine sulfoximine, buthionine sulfones, penta-, hexa-, heptathionine sulfoximine) in very low tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivates thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

The total concentration of antioxidants in the preparations of the present invention may, for example, be from about 0.001% to about 6% by weight, preferably from about 0.01% to about 3% by weight, e.g., from about 0.05% to about 2% by weight, based on the total weight of the preparation.

Non-limiting examples of advantageous active ingredients for incorporation into the preparations of the present invention include natural active ingredients and/or derivatives thereof, such as, for example, alpha-lipoic acid, phytoene, D-biotin, coenzyme Q10, alpha-glucosylrutin, carnitine, carnosine, natural and/or synthetic isoflavonoids, creatin, fumaric esters, ectoin and derivatives thereof, taurine and β-alanine.

Preparations according to the present invention which comprise, for example, known antiwrinkle active ingredients, such as flavone glycosides (in particular α-glycosylrutin), coenzyme Q10, vitamin E and/or derivatives and the like are particularly advantageously suitable for the prophylaxis and treatment of cosmetic or dermatological changes in the skin, as arise, for example, during skin ageing (such as, for example, dryness, roughness and formation of dryness wrinkles, itching, reduced regreasing (e.g. after washing), visible vascular dilations (teleangiectases, couperosis), flaccidity and formation of lines and wrinkles, local hyperpigmentation, hypopigmentation and incorrect pigmentation (e.g. age spots), increased susceptibility to mechanical stress (e.g. cracking) and the like). In addition, they are advantageously suitable for combating the appearance of dry and/or rough skin.

Other pharmaceutically or dermatologically effective substances, such as, for example, substances which calm and care for the skin, can also be incorporated into the preparations according to the present invention. These include, for example, panthenol, allantoin, tannin, antihistamines (e.g. loratadine, cetirizine, dimethindene, clemastine, capsaicin, $H_1$ antagonists, tannin preparations), local anaesthetics, opiate antagonists (e.g. naltrexone, naloxone), antiphlogistics, glucocorticoids (e.g. hydrocortisone, tacrolimus, cyclosporin A) and plant active ingredients, such as azulene and bisabolol, glycyrrhizin, hamamelin and plant extracts, such as camomile, aloe vera, hamamelis, liquorice. The vitamin $D_3$ analogues tacalcitol, calcipotriol, colecalciferol and calcitrol (vitamin $D_3$) and/or fumaric esters can also be advantageously incorporated into the preparations of the present invention.

The preparations of the present invention are also suitable for incorporating therein active ingredients for aiding the skin functions in dry skin such as, for example, vitamin C, biotin, carnitine, creatine, propionic acid, green tea extracts, eucalyptus oil, urea and mineral salts such as, for example, NaCl, sea minerals, and osmolytes such as, for example, taurine, inositol, betaine, quaternary ammonium compounds. In a similar way, the incorporation of active ingredients for alleviating or positively influencing irritative skin conditions, whether for sensitive skin in general or for skin irritated by noxae (UV light, chemicals) may be advantageous. In this regard, mention may be made of active ingredients such as sericosides, various extracts of licorice, licochalcones, in particular licochalcone A, silymarin, silyphos, dexpanthenol, inhibitors of prostaglandin metabolism, in particular of cyclooxygenase and of leukotriene metabolism, in particular of 5-lipoxygenase, but also of the 5-lipoxygenase inhibitor protein, FLAP. The incorporation of pigmentation modulators may also be advantageous. In this regard, mention may be made of active ingredients which reduce the pigmentation of the skin and thus lead to a cosmetically desired lightening of the skin, reduce the appearance of age spots and/or lighten existing age spots. Non-limiting examples of corresponding substances include tyrosine sulfate, dioic acid (8-hexadecene-1,16-dicarboxylic acid), and lipoic acid and liponamide, various extracts of licorice, kojic acid, hydroquinone, arbutin, alpha-arbutin, deoxyarbutin, bearberry (Uvae ursi), ursolic acid, ascorbic acid, green tea extracts, aminoguanidine, pyridoxamine.

Further, the preparations according to the present invention may comprise active ingredients which bring about an increased or more rapid tanning of the skin, be it with or without the effect of UV light, such as, e.g., Advanced Glycation Endproducts (AGE), lipofuscins, nucleic acid oligonucleotides, purines and pyrimidines, NO-releasing substances.

Non-limiting examples of advantageous moisturizers and humectants for use in the preparations of the present invention include sorbitol, mannitol, glycerol, lactic acid and/or lactates, in particular sodium lactate, butylene glycol, propylene glycol, biosaccharide gum-1, glycine soya, ethylhexyloxy glycerol, pyrrolidone carboxylic acid and urea. In addition, it may be advantageous to use polymeric moisturizers from the group of water-soluble and/or water-swellable and/or water-gellable poly-saccharides. Of particular advantage are, for example, hyaluronic acid, chitosan and/or a fucose-rich polysaccharide, which is filed in Chemical Abstracts under the registry number 178463-23-5 and is available, for example, under the name Fuco-gel®1000 from SOLABIA S.A.

The cosmetic or dermatological preparations according to the present invention may also comprise fillers which, for example, further improve the sensory and cosmetic properties of the formulation and bring about or enhance a velvety or silky feel on the skin. Advantageous fillers for the purposes of the present invention are starch and starch derivatives (such as, for example, tapioca starch, distarch phosphate, aluminum or sodium starch octenylsuccinate and the like), pigments which have neither primarily a UV filter effect nor a colouring effect (such as, for example, boron nitride etc.) and/or Aerosils® (CAS No. 7631-86-9).

UV filter substances which may be incorporated into the preparations of the present invention include those which are conventionally used in cosmetic or dermatological preparations. Non-limiting examples of advantageous UV filter substances for the purposes of the present invention are set forth below.

UV filter substances based on triazine derivatives of the general formula

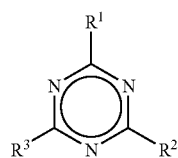

are known per se and are described, for example, in EP-A-775 698, EP-A-0 878 469 and EP-A-1 027 881, the entire disclosures whereof are incorporated by reference herein.

With respect to the $C_3$ axis of the triazine nucleus of these compounds, both symmetric and asymmetric substitution is possible. Substituted s-triazine derivatives have three identical substituents $R^1$, $R^2$ and $R^3$, whereas asymmetrically substituted s-triazine derivates have substituents of which at least two are different. In the following, asymmetrically substituted s-triazine derivatives will simply be referred to as "triazine derivtives".

Advantageous triazine derivatives include those which are described in EP-A-775 698 and have the general formula:

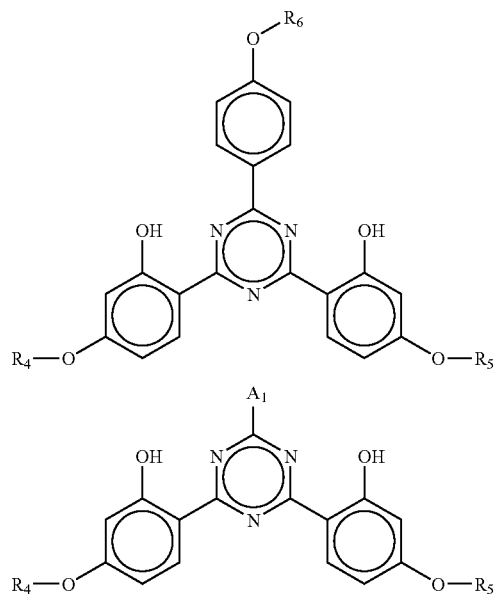

Particularly preferred substances are those wherein $R_4$ and $R_5$ represent branched or unbranched alkyl groups having from about 1 to about 18 carbon atoms. Advantageously, these alkyl groups may be substituted with silyloxy groups.

The group $A_1$ preferably represents a substituted homo- or heterocyclic aromatic ring having five or six ring members.

Particularly advantageous UV filter substances for the purposes of the present invention are the following s-triazine compounds:

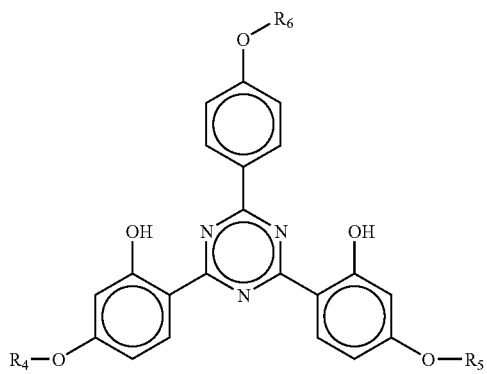

wherein $R_6$ represents hydrogen or a branched or unbranched alkyl group having from about 1 to about 10 carbon atoms, particularly 2,4-bis-{[4-(2-ethyl-hexyloxy)-2-hydroxy]-phenyl}-6-(4-methoxyphenyl)-1,3,5-triazine (INCI: Aniso Triazin) which is available under the trade name Tinosorb® S from CIBA-Chemikalien GmbH and has the following structure:

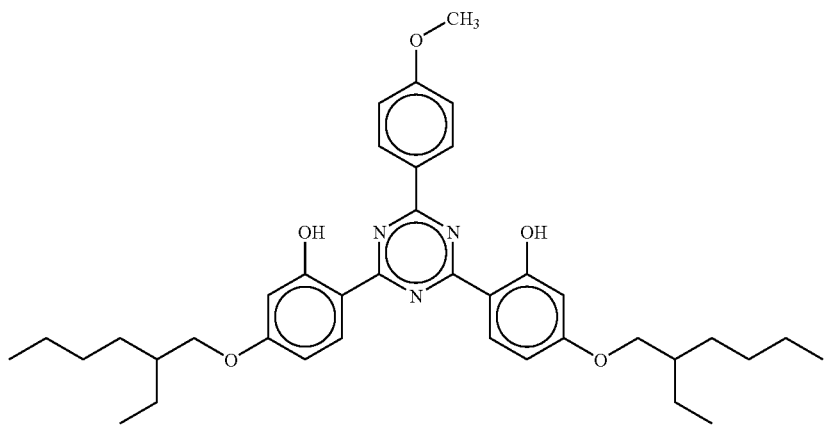

Another particularly advantageous asymmetrically substituted triazine derivative for the purposes of the present invention is dioctylbutylamidotriazone (INCI: Dioctyl-butamidotriazone), which is available under the trade name UVASORB HEB from Sigma 3V and has the following structure:

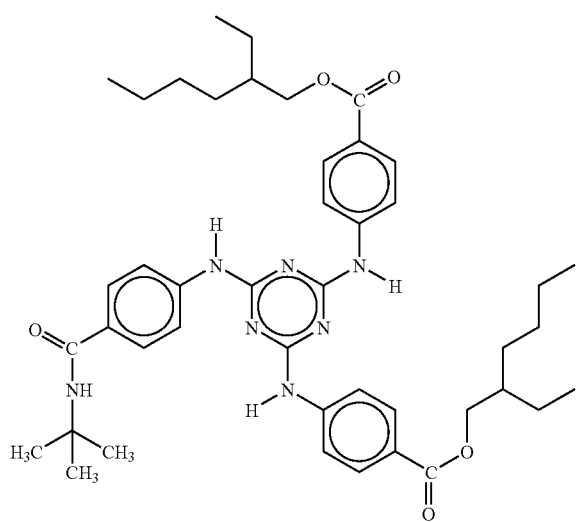

Further UV filter substances which are particularly advantageous for the purposes of the present invention include:
2,4-bis-{[4-(3-sulfonato)-2-hydroxy-propyloxy)-2-hydroxy]-phenyl}-6-(4-methoxyphenyl)-1,3,5-triazine sodium salt,
2,4-bis-{[4-(3-(2-propyloxy)-2-hydroxy-propyloxy)-2-hydroxy]-phenyl}-6-(4-methoxyphenyl)-1,3,5-triazine,
2,4-bis-{[4-(2-ethyl-hexyloxy)-2-hydroxy]-phenyl}-6-[4-(2-methoxyethyl-carboxyl)-phenylamino]-1,3,5-triazine,
2,4-bis-{[4-(3-(2-propyloxy)-2-hydroxy-propyloxy)-2-hydroxy]-phenyl}-6-[4-(ethylcarboxyl)-phenylamino]-1,3,5-triazine,
2,4-bis-{[4-(2-ethyl-hexyloxy)-2-hydroxy]-phenyl}-6-(1-methyl-pyrrol-2-yl)-1,3,5-triazine,
2,4-bis-{[4-tris(trimethylsiloxy-silylpropyloxy)-2-hydroxy]-phenyl}-6-(4-methoxyphenyl)-1,3,5-triazine,
2,4-bis-{[4-(2-methylpropenyloxy)-2-hydroxy]-phenyl}-6-(4-methoxyphenyl)-1,3,5-triazine and
2,4-bis-{[4-(1',1',1',3',5',5',5'-heptamethylsiloxy-2-methyl-propyloxy)-2-hydroxy]-phenyl}-6-(4-methoxyphenyl)-1,3,5-triazine.

A further example of an advantageous UV filter substance for use in the present invention is phenylene-1,4-bis-(2-benzimidazyl)-3,3'-5,5'-tetrasulfonic acid

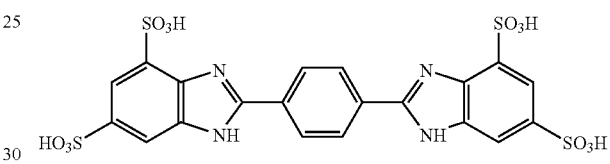

and the salts thereof, preferably the sodium, potassium- and triethanolammonium salts, in particular, the phenylene-1,4-bis-(2-benzimidazyl)-3,3'-5,5'-tetrasulfonic acid-bis-sodium salt

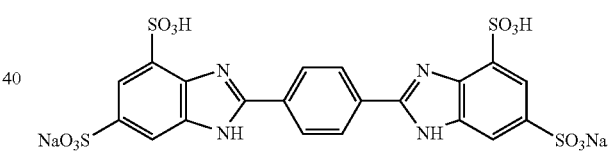

with the INCI name Bisimidazylate, which is available, for example, under the trade name Neo Heliopan AP from Haarmann & Reimer.

Another particularly advantageous UV filter substance for use in the present invention is 2,2'-methylen-bis-(6-(2H-benzotriazol-2-yl)-4-(1,1,3,3-tetramethylbutyl)-phenol) [INCI: Bisoctyltriazol] of the formula:

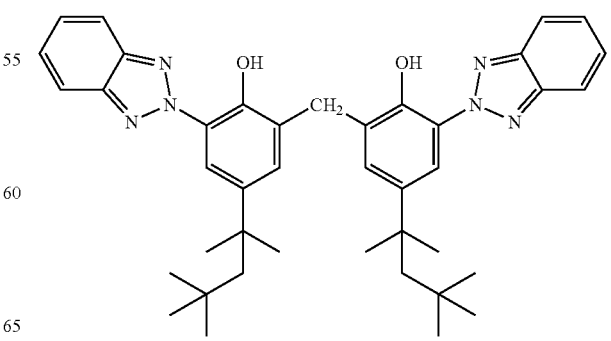

which is available under the trade name Tinosorb® M from CIBA-Chemikalien GmbH.

Of course, two or more filter substances can be used in combination. Particularly advantageous combinations of UV filter substances include:

2,4-bis-{[4-(2-ethyl-hexyloxy)-2-hydroxy]-phenyl}-6-(4-methoxyphenyl)-1,3,5-triazine and phenylene-1,4-bis-(2-benzimidazyl)-3,3'-5,5'-tetrasulfonic acid-bis-sodium salt; phenylene-1,4-bis-(2-benzimidazyl)-3,3'-5,5'-tetrasulfonic acid-bis-sodium salt and 2,2'-methylene-bis-(6-(2H-benzotriazol-2-yl)-4-(1,1,3,3-tetramethylbutyl)-phenol); 2,4-bis-{[4-(2-ethyl-hexyloxy)-2-hydroxy]-phenyl}-6-(4-methoxyphenyl)-1,3,5-triazine and 2,2'-methylene-bis-(6-(2H-benzotriazol-2-yl)-4-(1,1,3,3-tetramethylbutyl)-phenol); and 2,4-bis-{[4-(2-ethyl-hexyloxy)-2-hydroxy]-phenyl}-6-(4-methoxyphenyl)-1,3,5-triazine (Tinosorb® S), phenylene-1,4-bis-(2-benzimidazyl)-3,3'-5,5'-tetrasulfonic acid-bis-sodium salt (Neo Heliopan® AP) and 2,2'-methylene-bis-(6-(2H-benzotriazol-2-yl)-4-(1,1,3,3-tetramethylbutyl)-phenol) (Tinosorb® M).

Further UV filter substances which can advantageously be used in the preparations of the present invention include:

Oil-soluble UV-B filter substances such as, for example:
3-benzylidene camphor derivatives, preferably 3-(4-methylbenzylidene)camphor [INCI: 4-Methylbenzylidene Camphor], which is available from Merck under the trade name Eusolex 6300 and/or 3-benzylidene camphor;

4-aminobenzoic acid derivatives, preferably 2-ethylhexyl 4-dimethylamino-benzoate, amyl 4-dimethylaminobenzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 2-ethylhexyl 4-methoxybenzalmalonate;

symmetric triazine derivatives, preferably tris(2-ethylhexyl) 4,4',4"-(1,3,5-triazine-2,4,6-triyltriimino)-tris-benzoate [INCI: Octyl Triazone], which is available from BASF Aktiengesellschaft under the trade name UVINUL® T 150;

benzotriazole derivatives, preferably 2,2'-methylene-bis-(6-(2H-benzotriazol-2-yl)-4-(1,1,3,3-tetramethylbutyl)-phenol); and UV filters bound to polymers.

Advantageous water-soluble UV-B filter substances include:
salts of 2-phenylbenzimidazole-5-sulfonic acid, for example, the sodium, potassium and triethanolammonium salts, and the sulfonic acid itself;

sulfonic acid derivatives of benzylidene camphor, such as, e.g., 4-(2-oxo-3-bornylidenemethyl)benzolsulfonic acid, 2-methyl-5-(2-oxo-3-bornylidenemethyl)sulfonic acid and salts thereof.

Further examples of conventional UV-A filter substances which are suitable for use in the present include derivatives of dibenzoylmethane, in particular, 1-(4'-tert-butylphenyl)-3-(4'-methoxyphenyl)propane-1,3-dione and 1-phenyl-3-(4'-isopropyl-phenyl)propane-1,3-dione. Another advantageous UV-A filter substance is 4-(tert-butyl)-4'-methoxydibenzoylmethane (CAS-Nr. 70356-09-1), which is available from Givaudan under the trade name Parsol® 1789 and from Merck under the trade name Eusolex® 9020.

Also advantageous are 1,4-di(2-oxo-10-sulfo-3-bornylidenemethyl)benzene and the salts thereof (in particular, the 10-sulfato compounds, especially the sodium, potassium and triethanolammonium salts), which is also named benzene-1,4-di(2-oxo-3-bornylidenmethyl-10-sulfonic acid) and has the structure:

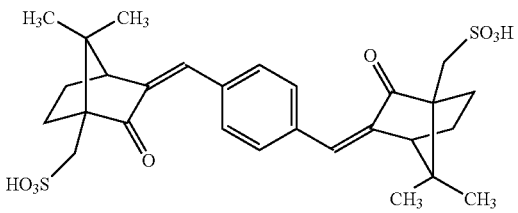

Advantageous filter substances which absorb both UV-A and UV-B radiation, so-called broadband filters, include 2,2'-methylene-bis-(6-(2H-benzotriazol-2-yl)-4-(1,1,3,3-tetramethylbutyl)-phenol) or 2-(2H-benzotriazol-2-yl)-4-methyl-6-[2-methyl-3-[1,3,3,3-tetramethyl-1-[(trimethylsilyl)oxy]disiloxanyl]propyl]-phenol (CAS-Nr.: 155633-54-8) with the INCI name Drometrizole Trisiloxane, which has the structure:

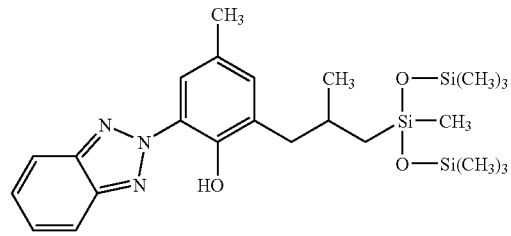

Certain salicylic acid derivatives such as, e.g., 4-isopropylbenzyl salicylate, 2-ethyl-hexylsalicylate (=Octylsalicylate), homomenthyl salicylate are also suitable UV filter substances.

Another filter substance which is suitable for use in the preparations of the present invention is ethylhexyl-2-cyano-3,3-diphenylacrylate (Octocrylen), which is available from BASF under the trade name Uvinul® N 539 and has the structure:

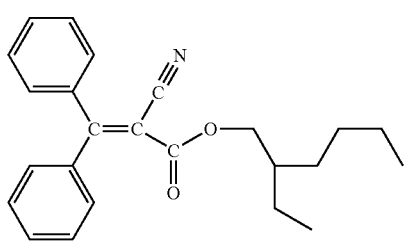 [SMILES: CCCCC(CC)COC(=O)C(C#N)=C(c1ccccc1)c1ccccc1]

Advantageous UV filter substances which are liquid at room temperature and can advantageously be used according to the present invention include homomenthyl salicylate, 2-ethylhexyl-2-cyano-3,3-diphenylacrylate, 2-ethylhexyl-2-hydroxybenzoate and esters of cinnamic acid, preferably 2-ethylhexyl 4-methoxy-cinnamate and isopentyl 4-methoxycinnamate.

Homomenthyl salicylate (INCI: Homosalate) has the structure:

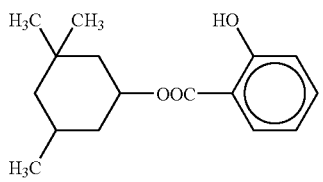

2-Ethylhexyl-2-cyano-3,3-diphenylacrylate (INCI: Octocrylene) is available from BASF under the trade name Uvinul® N 539 and has the structure:

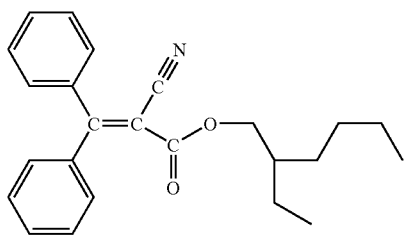 [SMILES: CCCCC(CC)COC(=O)C(C#N)=C(c1ccccc1)c1ccccc1]

2-Ethylhexyl 2-hydroxybenzoate (2-ethylhexyl salicylate, octyl salicylate, INCI: Octyl Salicylate) is available, for example, from Haarmann & Reimer under the trade name Neo Heliopan OS and has the structure:

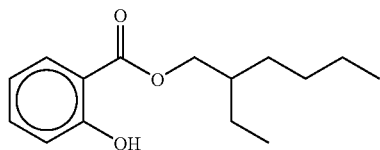

2-Ethylhexyl 4-methoxycinnamate (INCI: Octyl Methoxycinnamate) is available, for example, from Hoffmann-La Roche under the trade name Parsol MCX and has the structure:

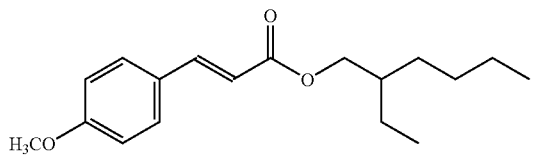 [SMILES: CCCCC(CC)COC(=O)/C=C/c1ccc(OC)cc1]

Isopentyl 4-methoxycinnamate (INCI: Isoamyl p-Methoxycinnamate) is available, for example, from Haarmann & Reimer under the trade name Neo Heliopan E 1000 and has the structure:

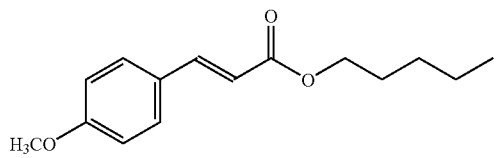 [SMILES: CCCCCOC(=O)/C=C/c1ccc(OC)cc1]

The total amount of UV filter substances in the preparations of the present invention will usually be from about 0.1% to about 30% by weight, based on the total weight of the preparation. Preferably, the amount will be at least about 0.5%, e.g., at least about 1% by weight, and not higher than about 20%, e.g., not higher than about 15% by weight.

Preferred pigments as optional components of the preparations of the present invention include metal oxides and other metal compounds which are insoluble or sparingly soluble in water, in particular oxides of titanium ($TiO_2$), iron (e.g. $Fe_2O_3$, $Fe_3O_4$, FeO(OH)), zirconium ($ZrO_2$), silicon ($SiO_2$), manganese (e.g. MnO), aluminum ($Al_2O_3$), cerium (e.g. $Ce_2O_3$), tin (SnO), mixed oxides of the corresponding metals, and mixtures of such oxides, mica, and barium sulphate ($BaSO_4$). Optionally, these pigments may be surface-treated.

The dyes which are suitable for use in the preparations of the present invention may be chosen, for example, from the corresponding positive list of cosmetics legislation or the EC list of cosmetic colorants. In most cases, they are identical to the dyes that are approved for foodstuffs. Advantageous dyes are, for example, carmine, Prussian blue, chromium oxide green, ultramarine blue and/or manganese violet.

The pH of the preparations of the present invention can be adjusted in a known manner by adding acids or bases, preferably by adding buffer substances, e.g. based on citric acid/citrate or phosphoric acid phosphate buffer mixtures. The pH is preferably below about 10, e.g. in the range of from about 2 to about 7, in particular from about 3 to about 5.

To apply the preparations of the present invention, conventional containers and devices for cosmetic or dermatological preparations can be used. For example, if the preparations are present in the form of a gel, a stick or a viscous liquid, stick dispensers, gel dispensers, tubes and roll-ons are particularly preferred. If the preparations are transparent or translucent and/or comprise suspended particles, preference is given to translucent, clear containers through which the preparations are visible.

Especially in cases where the preparation comprises suspended particles, particularly advantageous applicators include those which are described in DE 100 47 448, the entire disclosure whereof is expressly incorporated by reference herein.

Specifically, an applicator according to DE 100 47 448 is a roll-on applicator which includes a rotatable and rotationally symmetric geometric body (e.g., a ball or a roll) which has a structured surface (e.g., indentations on the surface thereof. The body is in contact with a reservoir for the cosmetic or dermatological preparation and by being rotated, it transports the preparation from the reservoir onto the skin that is contacted by the body. The indentations on the surface of the body are preferably distributed symmetrically and may comprise, for example, channels, grooves, notches, round indentations, any combinations thereof, etc. The depth of the indentations and/or the distance between the body and a fitment surrounding the circumference of the body may be adjusted as a function of the size(s) of the particles that are suspended in the preparation so that they are large enough to allow the particles to be transported from the reservoir (usually a container of the type mentioned above) to the surface of the rotatable body which comes into contact with the skin.

The preparations of the present invention can be stored and dispensed from any suitable container, e.g., a container which is usually used for cosmetic products such as, e.g., a bottle. The container materials may, for example, be those which are used conventionally for cosmetics such as, e.g. glass, plastics (polypropylene, polyethylene, polyethylene terephthalate, etc.) metal and the like. In this regard, it has been found that if the container is transparent (which is preferred according to the present invention), the preparations of the present invention may be subject to light-induced degradation, wherefore it is preferable in this case to incorporate a light stabilizer and/or UV filter into the preparations. Surprisingly, it has been found that by using a glass container the problem of light-induced degradation can be substantially eliminated.

EXAMPLES

In the following Examples the numbers indicate the amounts of the individual components in percent by weight based on the total weight of the preparation.

| | Example No. | | |
|---|---|---|---|
| | 1 | 2 | 3 |
| Activated aluminum chlorohydrate | 5 | 10 | 10 |
| Mandelic acid | 1.4 | 1.8 | 2 |
| Sodium citrate | — | — | 1 |
| Water | 93.6 | 88.2 | 87 |
| Total | 100 | 100 | 100 |

| | Example No. | | |
|---|---|---|---|
| | 4 | 5 | 6 |
| Glyceryl isostearate | 2.6 | 2.5 | 2.5 |
| Isoceteth-20 | 5 | 5 | 5 |
| PEG-150 distearate | 1 | 1.5 | 0.7 |
| Dicaprylyl ether | 5 | 5 | 5 |
| Mandelic acid | 1.5 | 1.5 | 2 |
| Activated aluminum chlorohydrate | 10 | 10 | 10 |
| Perfume | 1 | 1 | 1 |
| Butylene glycol | 3 | — | 3 |
| Methylparaben | 0.2 | 0.2 | — |
| Water | 70.7 | 73.3 | 70.8 |
| Total | 100 | 100 | 100 |

| | Example No. | | |
|---|---|---|---|
| | 7 | 8 | 9 |
| Activated aluminum chlorohydrate (AACH) | — | 5 | — |
| Aluminum chlorohydrate (ACH) | 5 | 5 | 10 |
| Mandelic acid | 1.4 | 1.8 | 2 |
| Sodium citrate | — | — | 1 |
| Water | 93.6 | 88.2 | 87 |
| Total | 100 | 100 | 100 |

| | Example No. | | |
|---|---|---|---|
| | 10 | 11 | 12 |
| Glyceryl isostearate | 2.6 | 2.5 | 2.5 |
| Isoceteth-20 | 5 | 5 | 5 |
| PEG-150 distearate | 1 | 1.5 | 0.7 |
| Dicaprylyl ether | 5 | 5 | 5 |
| Mandelic acid | 1.5 | 1.5 | 2 |
| Activated aluminum chlorohydrate (AACH) | 1 | — | 5 |
| Aluminum chlorohydrate (ACH) | 8 | 10 | 5 |
| Perfume | 1 | 1 | 1 |
| Butylene glycol | 3 | — | 3 |
| Methylparaben | 0.2 | 0.2 | — |
| Water | 71.7 | 73.3 | 70.8 |
| Total | 100 | 100 | 100 |

Example 13

| | |
|---|---|
| PEG-40 Hydrogenated Castor Oil | 5.0 |
| Perfume | 1.0 |
| Mandelic Acid | 3.2 |
| Activated aluminum chlorohydrate | 10.0 |
| Water | 80.8 |

Example 14

| | |
|---|---|
| Aluminum Chlorohydrate | 20.00 |
| Disodium EDTA | 0.10 |
| Fragrance | 1.00 |
| Mandelic Acid | 2.20 |
| PEG-40 Hydrogenated Castor Oil | 5.00 |
| Water | 71.70 |

Example 15

Preparation of Clear Gel with Gas Bubbles Incorporated Therein

Materials

Component A: 2.2 g of mandelic acid in 70.8 g of water (mandelic acid and water stirred for 15 minutes with a magnetic stirrer at room temperature)

Component B: 1.0 g of perfume in 5.0 g of PEG 40 hydrogenated castor oil

Component C: 20.0 g of aqueous ACH solution (20% by weight)

Component D: aqueous trisodium EDTA solution (20% by weight).

Procedure

1. Add Component A to Component B and stir for 20 minutes at room temperature (200 min$^{-1}$; paddle stirrer RW 20 DZM.n, 72 W, IP 20/KL 0 from IKA Labortechnik, Beme, Switzerland) until a clear solution is formed.

2. Add Component C to solution and stir at room temperature for 45 minutes.

3. Add Component D and stir at room temperature for 15 minutes.

The resultant mixture is further processed with one of the following devices to incorporate air bubbles therein:

(a) "Zauberstab" from ESGE, Germany (Model SG 2000, 200 watts, KB 5 min.): 5 sec at Setting 1 and 10 min at Setting 2;

(b) Ultraturrax (IKA T 50 basic, 100 watts, IP 21): 2 minutes at 5,200 min$^{-1}$;

(c) Homocenta (Model S100 LS90, 2 PS) 2810 min$^{-1}$; mixture is passed through the device twice;
(d) The mixture is also treated with compressed air: 30 sec at 3 L/min and 1.5 min at 2-5 L/min.

The following devices and methods for incorporating air bubbles do not afford satisfactory results:
(i) Kitchen Aid Classic (Model KSM 45, 250 watts, 10 min.) 2.5 min at Setting 4 and 10 min at Setting 4.5 (basket stirrer);
(ii) propeller stirrer at 300 min$^{-1}$;
(iii) dissolver at 200 min$^{-1}$;
(iv) "Khiet" stirrer at 200 min$^{-1}$.

Example 16

Preparation of Clear Gel with Beads Incorporated Therein

Materials
Component A: 2.2 g of mandelic acid in 70.5 g of water (stir for 20 minutes at 25° C.)
Component B: 1.0 g of perfume in 5.0 g of PEG 40 hydrogenated castor oil (stir for 20 minutes at 25° C.)
Component C, 20.0 g of aqueous ACH solution (20% by weight)
Component D: aqueous trisodium EDTA solution (20% by weight)
Component E: 0.3 g of beads.
Procedure
1. Add Component B to Component A and mix for 20 minutes at 25° C. (0.5 m/s; mixer Becomix 15 CD from A. Berents GmbH & Co. KG, Stuhr, Germany).
2. Add Component C and stir at 25° C. for 60 minutes.
3. Add Component D and stir at 25° C. for 10 minutes.
4. Add Component E and stir at 25° C. for 10 minutes.

As beads (component E) the following commercially available products are employed:
(1) Cosmospheres GMM-S (made by Pelletech Ltd., Switzerland; diameter 1.1-1.5 mm; green; comprising mannitol, microcrystalline cellulose, CI 77289 (Chromium Hydroxide Green) and lactic acid);
(2) Cosmospheres BMM-M (made by Pelletech Ltd., Switzerland; diameter 1.1-1.5 mm; blue; comprising mannitol, microcrystalline cellulose, CI 74160 (Pigment Blue 15) and lactic acid);
(3) Beads Cosmo YS-S (made by Pelletech Ltd., Switzerland; diameter 0.5-1.0 mm; yellow; comprising lactose, microcrystalline cellulose, *Helianthus Annuus* and CI 77492);
(4) Unispheres RP-572 (available from Induchem AG, Switzerland; diameter 0.5-0.9 mm; pink; comprising lactose, cellulose, hydroxypropylmethylcellulose, panthenyl triacetate, CI 73360); Unispheres UE-507 (available from Induchem AG, Switzerland; diameter 0.5-0.9 mm; purple; comprising lactose, cellulose, hydroxypropylmethylcellulose, tocopheryl acetate, CI 77007 (Pigment Blue 29);
(5) Cosmospheres Beads BCG2-L (made by Pelletech Ltd., Switzerland; diameter 1.5-2.0 mm; blue, glittering; comprising lactose, polyethylene terephthalate, microcrystalline cellulose, Acrylates Copolymer and Pigment Blue 15) and Cosmospheres Beads WCG-G-C-L (made by Pelletech Ltd., Switzerland; diameter 1.5-2.0 mm; gold, glittering; comprising lactose, polyethylene terephthalate, microcrystalline cellulose, shellac, Acrylates Copolymer, mica, titanium dioxide and iron oxides).

Example 17

Preparation of Clear Gel with Gas Bubbles Incorporated Therein

Materials
Component A: 2.2 kg of mandelic acid in 70.8 kg of water (stir at 25° C. for 45 minutes at 18 min$^{-1}$ and for 2 minutes at 2320 min$^{-1}$; Krieger MMU-100 from Krieger AG, Muttenz, Switzerland)
Component B: 1.0 kg of perfume in 5.0 kg of PEG 40 hydrogenated castor oil (stir for 2 minutes at 25° C. and 18 min$^{-1}$; Krieger MMU-100)
Component C, 20.0 g of aqueous ACH solution (20% by weight)
Component D: aqueous trisodium EDTA solution (20% by weight).
Procedure
1. Add Component B to Component A and stir for 24 minutes at 25° C. (at 18 min$^{-1}$; Krieger MMU-100)
2. Add Component C and stir at 25° C. for 60 minutes.
3. Add Component D and stir at 25° C. for 10 minutes.
4. Homogenize at 25° C. for 8 minutes at 2320 min$^{-1}$; Krieger MMU-100).
5. Keep at 25° C. for 2 hours.
6. Process with Hansa Mixer (Hansa Industrie-Mixer GmbH & Co KG, Stuhr, Germany) under the following conditions:

| | |
|---|---|
| Mixer head | 600 min$^{-1}$ |
| Pump | 120 L/h |
| Air Pre-pressure | 6.9 bar |
| Amount of Gas | 0.4 NL/min |
| System Pressure | 0.7 bar |
| Temperature in | 24.0° C. |
| Overrun (theory) | 15% |
| Overrun (actual) | 8.19%. |

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:
1. A cosmetic or dermatological preparation, wherein the preparation comprises (a) at least one antiperspirant active ingredient, (b) at least one α-hydroxycarboxylic acid, and (c) at least 60% by weight of water, based on a total weight of the preparation, and wherein the preparation further comprises a plurality of suspended liquid particles, at least 80% of the suspended particles having a size of from about 0.5 mm to about 5 mm.

2. The preparation of claim 1, wherein the liquid particles comprise an emulsion.

3. The preparation of claim 1, wherein the suspended particles are colored.

4. The preparation of claim 1, wherein (b) comprises at least one of mandelic acid, tartaric acid, and citric acid.

5. The preparation of claim 4, wherein (b) comprises at least mandelic acid.

6. The preparation of claim 5, wherein (a) comprises one or more aluminum salts.

7. The preparation of claim 1, wherein (a) comprises aluminum chlorohydrate.

8. The preparation of claim 1, wherein (a) comprises activated aluminum chlorohydrate.

9. The preparation of claim 1, wherein (a) comprises both aluminum chlorohydrate and activated aluminum chlorohydrate.

10. The preparation of claim 1, wherein a weight ratio (a):(b) is from about 15:1 to about 1:1.

11. The preparation of claim 10, wherein a weight ratio (a):(b) is from about 12:1 to about 2:1.

12. The preparation of claim 1, wherein (a) is present in an amount of from about 1% to about 25% by weight, based on the total weight of the preparation.

13. The preparation of claim 1, wherein (b) is present in an amount of from about 0.1% to about 10% by weight, based on the total weight of the preparation.

14. The preparation of claim 1, wherein the preparation further comprises at least one of EDTA and a salt thereof.

15. The preparation of claim 1, wherein the preparation is present as an O/W microemulsion.

16. The preparation of claim 15, wherein the microemulsion comprises one or more emulsifiers which are at least one of polyethoxylated and polypropoxylated.

17. The preparation of claim 1, wherein the preparation is present as a gel.

18. The preparation of claim 1, wherein the preparation has a defined yield point.

19. The preparation of claim 18, wherein the preparation has a yield point, determined at 25° C. with a shear stress time ramp of 40 Pa/min, of from about 5 Pa to about 120 Pa.

20. The preparation of claim 1, wherein the preparation is transparent or translucent.

21. The preparation of claim 1, wherein the preparation further comprises a sunscreen.

22. The preparation of claim 1, wherein the preparation further comprises a perfume and a solubilizer for the perfume.

23. The preparation of claim 22, wherein the solubilizer comprises a polyalkoxylated fatty acid triglyceride.

24. The preparation of claim 1, wherein the preparation comprises at least 70% by weight of (c).

25. The preparation of claim 1, wherein the preparation is present as an emulsion.

26. The preparation of claim 1, wherein at least 90% of the suspended particles have a size of from about 0.5 mm to about 5 mm.

27. The preparation of claim 1, wherein the suspended particles have a particle size of up to 3 mm.

28. The preparation of claim 27, wherein the suspended particles have a particle size of at least 0.5 mm.

29. A cosmetic or dermatological preparation, wherein the preparation comprises (a) at least one of aluminum chlorohydrate and activated aluminum chlorohydrate, (b) mandelic acid, and (c) at least 70% by weight water, based on a total weight of the preparation, and wherein the preparation further comprises a plurality of suspended liquid particles, at least 80% of the suspended particles having a size of from about 0.5 mm to about 5 mm.

30. The preparation of claim 29, wherein a weight ratio (a):(b) is from about 10:1 to about 2.5:1.

31. The preparation of claim 29, wherein the preparation comprises from about 1% to about 20% by weight of (a) and from about 0.1% to about 8% by weight of (b), based on the total weight of the preparation.

32. The preparation of claim 29, wherein the preparation is present as an emulsion.

33. The preparation of claim 31, wherein the preparation is present as an O/W microemulsion.

34. The preparation of claim 31, wherein the preparation is present as a microemulsion gel.

35. A cosmetic or dermatological preparation, wherein the preparation comprises (a) from about 1% to about 20% by weight of at least one of aluminum chlorohydrate and activated aluminum chlorohydrate, (b) from about 0.1% to about 8% by weight of mandelic acid, a weight ratio (a):(b) being from about 10:1 to about 2.5:1, and (c) at least 70% by weight of water, each based on a total weight of the preparation, and wherein the preparation further comprises a plurality of suspended liquid particles having a size of from about 0.5 mm to about 2 mm.

36. The preparation of claim 35, wherein the preparation is present as an O/W microemulsion gel.

37. A combination of the preparation of claim 1 and an applicator for the preparation, wherein the applicator is suitable for applying the preparation onto skin and comprises a rotatable and rotationally symmetric body with a structured surface.

38. The combination of claim 37, wherein the symmetric body comprises a ball.

* * * * *